United States Patent [19]

Metala et al.

[11] Patent Number: 4,746,858
[45] Date of Patent: May 24, 1988

[54] NON DESTRUCTIVE TESTING FOR CREEP DAMAGE OF A FERROMAGNETIC WORKPIECE

[75] Inventors: Michael J. Metala; William G. Clark, Jr., both of Murrysville; Warren R. Junker, Monroeville, all of Pa.

[73] Assignee: Westinghouse Electric Corp., Pittsburgh, Pa.

[21] Appl. No.: 2,538

[22] Filed: Jan. 12, 1987

[51] Int. Cl.$^4$ .................. G01R 33/12; G01N 27/72; G01N 27/90
[52] U.S. Cl. .................. 324/200; 73/779; 324/209; 324/228; 324/234
[58] Field of Search ........ 324/200, 202, 209, 226–228, 324/234, 236–240; 73/779, 822

[56] References Cited

U.S. PATENT DOCUMENTS

| | | | |
|---|---|---|---|
| 3,427,872 | 2/1969 | Leep et al. | 324/209 X |
| 4,418,315 | 11/1983 | Edwards et al. | 324/202 |
| 4,460,869 | 7/1984 | Buser et al. | 324/227 |
| 4,528,856 | 7/1985 | Junker et al. | 324/209 X |
| 4,533,095 | 11/1985 | Schenk et al. | 324/230 |
| 4,599,563 | 7/1986 | Tiitto et al. | 73/779 X |

Primary Examiner—Gerard R. Strecker

[57] ABSTRACT

Rapid nondestructive testing of a ferromagnetic workpiece for creep damage is carried out by placing an eddy current coil adjacent to the workpiece, passing an alternating current through the coil, measuring the eddy current response as influenced by the workpiece, and comparing the current measurement to a current calibrated to known creep damage for the given ferromagnetic material. Correlations of the eddy current response to creep rate and time to failure are generated from creep rupture tests performed on specimens of the given material subjected to varying conditions of time, temperature and stress. Qualitative tests can also be performed to identify the point of greatest creep damage by passing the eddy current coil over the workpiece to find the location of the lowest eddy current response. Conventional creep damage tests can then be performed at that location if desired.

9 Claims, 4 Drawing Sheets

NON DESTRUCTIVE TESTING FOR CREEP DAMAGE OF A FERROMAGNETIC WORKPIECE

BACKGROUND OF INVENTION

1. Field of Invention

This invention relates to a method of nondestructive testing of ferromagnetic workpieces and more particularly to such a method which utilizes eddy current testing for creep damage assessment.

2. Background Information

Prolonged exposure of ferromagnetic materials to mechanical stress and elevated temperatures may result in grain boundary migration of the alloying constituents which eventually leads to boundary failure and rupture of the material. This phenomenon, which is known as creep damage, is of particular concern in the power generation industry where efforts to extend plant life are dependent on the availability of accurate knowledge of the critical time and service dependent properties of the hardware of interest, such as high temperature creep degradation of structural steels.

Creep damage in alloy steels is a time, temperature, and strain dependent phenomenon which involves progressive detrimental changes in the inherent microstructure of the material. Simply stated, alloy steels are strengthened by thermal treatments that result in nonequilibrium conditions. When exposed to sufficiently high temperatures and stresses for long times, the nonequilibrium state will diminish with a corresponding decrease in load carrying ability. The degradation in mechanical properties associated with creep damage is a direct reflection of carbide chemistry and related dynamics. Features such as carbide composition, morphology, distribution and concentration control the creep properties. Beyond carbide chemistry considerations, void formation and cracking at the grain boundaries contribute to creep damage.

One current method of assessing creep damage of hardware exposed to prolonged stress at elevated temperatures is surface examination. The location to be tested, usually about ¼ to ½ inch in diameter, is ground to a depth of about 10 mils and etched in preparation for the taking of photomicrographs which are then analyzed to determine the condition of the grain boundaries. A related alternative to direct surface examination involves the replication of the surface with an acetate film and the subsequent laboratory examination of the film. Another current method of testing for creep damage requires hogging out a boar sample, typically about a sixteenth of an inch in diameter and a quarter inch long for metalographic analysis. A third common method used to estimate the potential creep damage to components exposed to years of service is the microminature mechanical test where again a small test coupon is hogged out of the material and subjected to tensile tests. These tests, while sometimes used successfully, have a major disadvantage in that they yield data for a given location only, such that the considerable knowledge required to properly select the appropriate test site is as important as the test itself. Of course, the boat sample and miniature test coupon approach are not non-destructive and yield undesirable notches that must be carefully blended to minimize stress concentrations.

Eddy current testing for flaws such as cracks or pitting in components subjected to extended service is in common usage. A coil of wire to which an alternating current is applied is placed adjacent to the workpiece so that the workpiece influences the impedance of the coil. As the coil is passed along the workpiece, flaws create characteristic variations in coil current which highly trained technicians have learned to recognize. Recently, eddy current techniques have been used to measure stress in ferromagnetic materials as described in U.S. Pat. No. 4,528,856 and to measure the thickness of a layer of a weakly ferromagnetic material on a ferromagnetic base as disclosed in U.S. Pat. No. 4,553,095. Both of these techniques utilize a flat pancake type coil which is provided with a magnetic bias.

There still remains a need for a rapid, non-destructive method of estimating creep damage in ferromagnetic materials subjected to years of service.

SUMMARY OF INVENTION

This and other objects are realized by the invention which takes advantage of the fact that elevated temperature creep damage in ferrous alloys manifests itself as grain boundary degradation which results in changes in the electromagnetic properties of the alloy in a manner roughly related to the extent of damage. Thus, the invention is directed to a method of non-destructive testing for creep damage in a ferromagnetic workpiece which includes applying an alternating current to an eddy current coil placed adjacent to the workpiece, measuring the current as influenced by the condition of the workpiece, and comparing the current measurement with current calibrated to known creep damage in the type of material of which the workpiece is made.

The correlation between measured current through the eddy current coil and creep damage in a specified material can be generated by measuring coil current for a series of specimens with known creep damage. The known creep damage can be measured by mechanical tests to provide the required quantitative evaluation of creep damage in the given material.

It has been found that more consistent measurements of creep damage can be obtained by applying a constant magnet bias to the portion of the workpiece being tested. Experiments with and without magnetic bias show that either approach reflects creep damage, but the magnetic bias reduces variations in eddy current results associated with inherent variations in magnetic permeability typical of all ferromagnetic materials.

The method of the invention can also be used to determine the locations where the prior art techniques of surface examination, surface replication, boat sample testing or microminiture mechanical coupon testing are to be conducted, by moving the eddy current coil over the workpiece. Since it has been found that creep damage alters the magnetic permeability of ferromagnetic steel, the location on the workpiece at which the eddy current response is most changed, is the location of greatest creep damage. This location can then be tested, if desired, by any of the prior art techniques.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
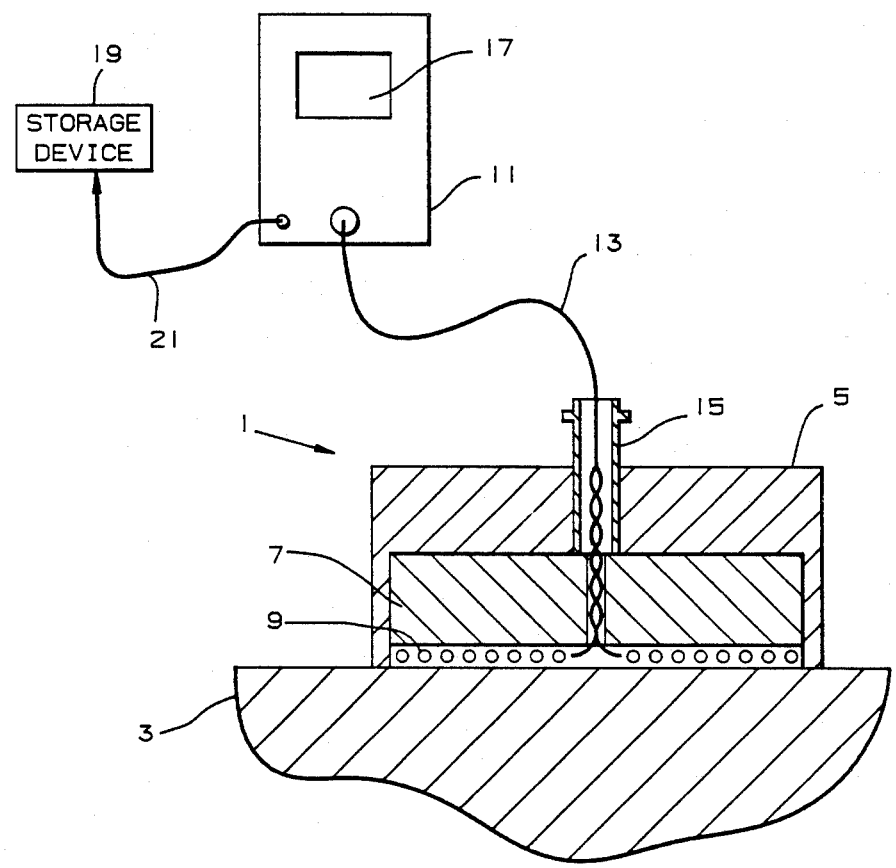
FIG. 1 illustrates apparatus for carrying out the method of the invention.

FIG. 1 illustrates apparatus suitable for carrying out the method of the invention. An eddy current probe 1 is placed adjacent the ferromagnetic workpiece 3 to be tested. A suitable probe is disclosed in commonly owned U.S. Pat. No. 4,528,856. This probe 1, enlarged in FIG. 1 to better show the details, includes a cup-shaped, cylindrical soft ion probe body 5 which houses a permanent magnet 7 and a flat, pancake type eddy current coil 9 positioned between the permanent magnetic 7 and the workpiece 3. Alternating current is supplied to the coil 9 by a signal generator and processor 11 through a cable 13. The cable 13 passes through a connector 15 secured in a central aperture in the probe body 5.

The signal generator and processor 11 supplies alternating current of a selected frequency to the coil 9 and presents a visual representation of the current as influenced by the workpiece on a visual display 17. Current readings can also be recorded in a storage device 19 connected to the signal generator and processor 11 by a cable 21. There are many eddy current test instruments suitable for use as the signal generator and processor 11, such as the Nortec NDT-25, or the Zetec MIZ 17.

Figure 2:
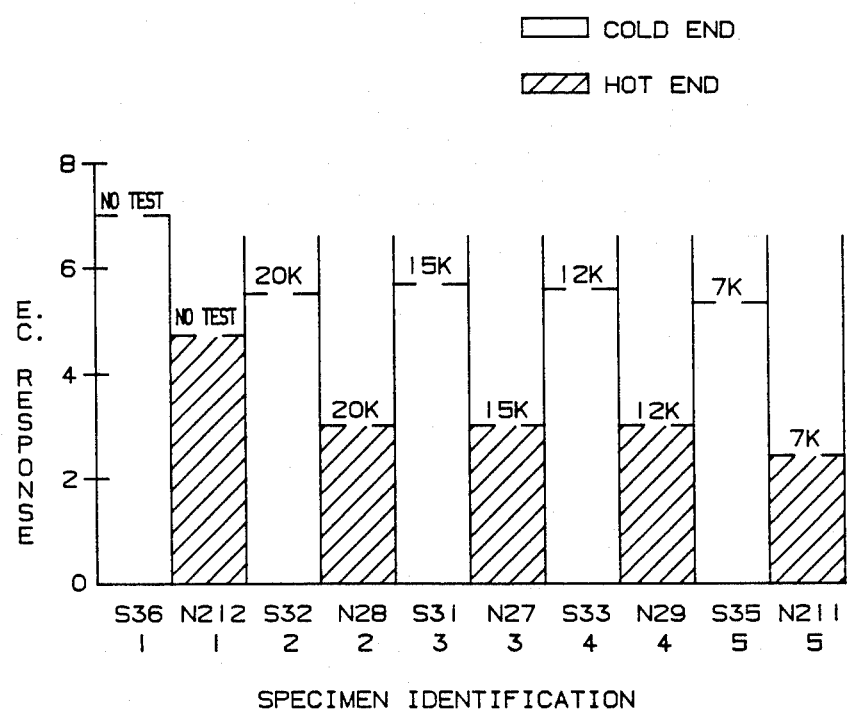
FIG. 2 is a graphical representation of the results of creep tests performed in accordance with the inventions on specimens with known creep damage.

In order to assess the ability of the eddy current probe to detect and characterize creep damage, standard samples from a steam header made of 1-$\frac{1}{4}$Cr-$\frac{1}{2}$Mo (ASME P-11) steel which had been exposed to both "hot" and "cold" service conditions for more than twenty-five years were tested. The results of the test are shown in bar graph form in FIG. 2. The results obtained from samples from the hot regions are shown crosshatched while those from the cold regions are uncrosshatched. The alphanumeric designation under each sample identifies the location on the standard header sample from which the specimen was taken. This header has become a reference standard by which creep damage in similar utility industry components is assessed.

The numerals 1 to 5 under the alphanumeric designation identify paired samples from corresponding regions at the hot and cold ends of the standard header. Thus, the sample S36 was taken from a location in the cold region symmetrical to the location in the hot region from which the sample N212 was taken. The graph of FIG. 2 also indicates data generated on creep test coupons for all of the samples, except the first pair, which in addition to the 25 years of service exposure, were tested for many hundreds of hours in the creep temperature range at the applied stress levels shown in FIG. 2. The stresses indicated were applied to the samples at 1000 degrees Fahrenheit until the samples ruptured. The times to failure of the corresponding hot and cold samples subjected to the same stress and temperature served as a measure of creep damage sustained during service. The ends of the samples unstressed by the rupture test, and therefore having creep damage resulting from hot and cold service as the case may be, were then tested using the eddy current probe to generate the current readings represented in FIG. 2. It is clear that in every case the eddy current response is lower on the hot end samples which were exposed to more creep damage.

Figure 3:
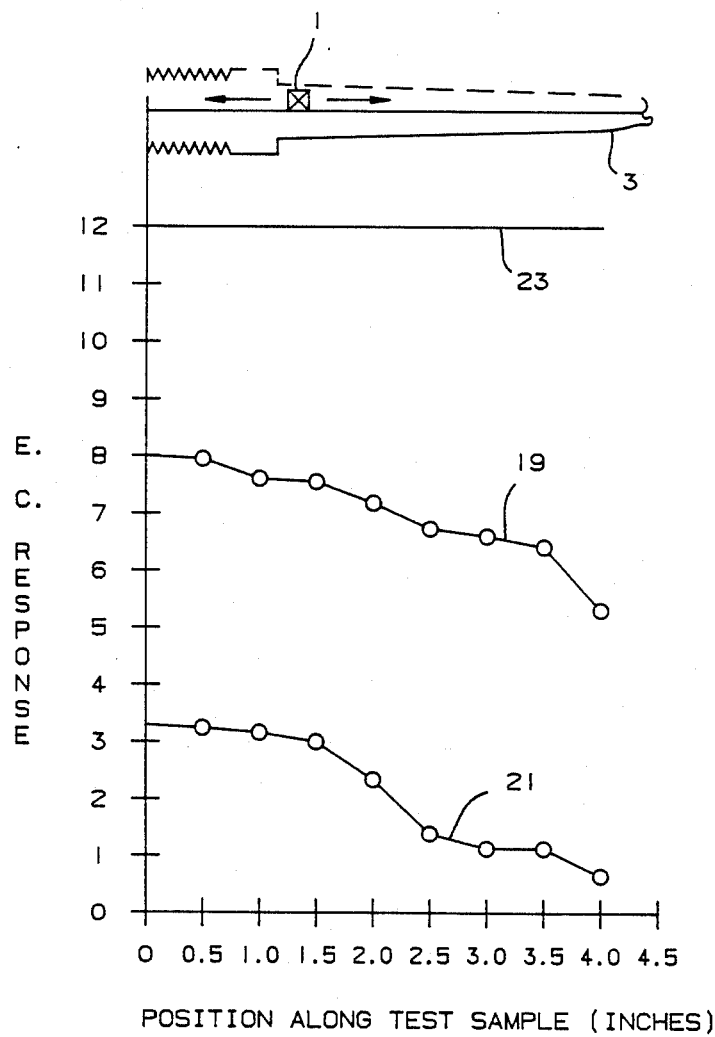
FIG. 3, is a composite drawing of a test specimen and the results of tests performed on several such specimens exposed to different conditions of time, temperature and stress.

To further assess the ability of the eddy current probe 1 to detect and characterize creep damage, creep rupture samples 3 from symmetrical locations on the standard ASME P-11 header subjected to hot and cold service were cut along the axial center lines and eddy current measurements were made along the axes as shown at the top of FIG. 3. The samples were necked down slightly to assure that rupture would occur in the desired areas. The trace 19 in FIG. 3 represents the eddy current response for the sample exposed to "cold" service while the trace 21 shows the response of the "hot" sample. An additional trace 23 illustrates the response of a new sample never exposed to loading. The results represented by FIG. 3 illustrate that the eddy current response is always lower for the "hot" sample than the "cold", and that the eddy current value decreases from the threaded end to the necked down point of fracture 25. The latter behavior reflects the increase in creep damage with the increase in stress from the loading end 27 to the point of fracture 25. The impact of 25 years of both "hot" and "cold" service is illustrated by the significant difference in eddy current response between the samples removed from service and represented by the traces 21 and 19 respectively, and the new sample represented by the trace 23.

A prominent diagnostic concept for the assessment of creep damage is based on the development of a correlation between creep properties (expressed as creep rate or time to rupture) and microstructural appearance (carbide morphology). Both carbide analysis and surface replication diagnostic methods depend upon this hypothesis. The characterization of creep damage proposed by this invention replaces the metallographic examination required by the carbide analysis and replication techniques with quantitative measurement of microstructural features through the use of eddy current test methods.

Figure 4A:
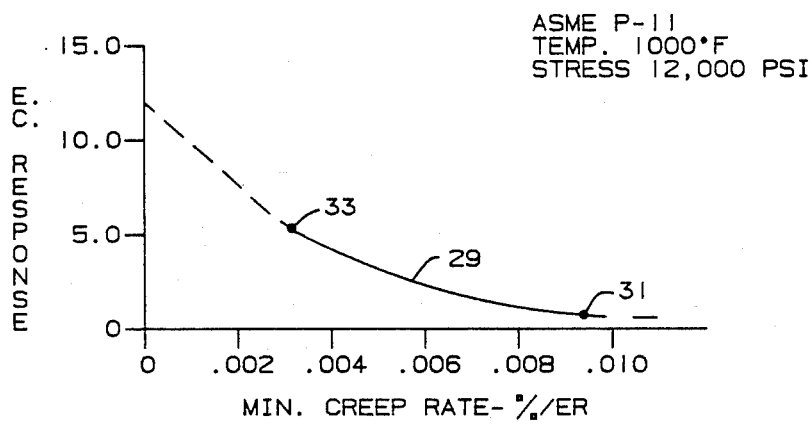
FIGS. 4a and 4b are plots of correlations in accordance with the invention of eddy current readings to creep rate and time to failure, respectively, for an exemplary ferromagnetic material.

A correlation of eddy current response with creep properties (creep rate or time to rupture) is required for quantitative measurements. FIGS. 4a and b present creep behavior versus eddy current response correlations based on data developed from the tests used to create FIG. 3. From such data, eddy current measurements made on the clean surface (dust blasted) of an actual component can be compared with the calibration and the creep damage predicted.

In order to make such a correlation, calculations were made from the data generated by the creep rupture tests performed on the "hot" and "cold" samples used in the tests of FIG. 3. In these tests, uniaxial tensile specimens were subjected to 12,000 psi stress at 1000 degrees Fahrenheit for several thousand hours until failure. Stretch as a function of time was measured in accordance with the American Society for Testing and Materials specification ASTM E 139 (10) to determine creep rate. After failure, eddy current tests were made on the threaded end of the specimens at which they were supported, where of course, creep damage remained at the level inflicted by prior service of the specimen and was unaffected by the test.

Figure 4B:
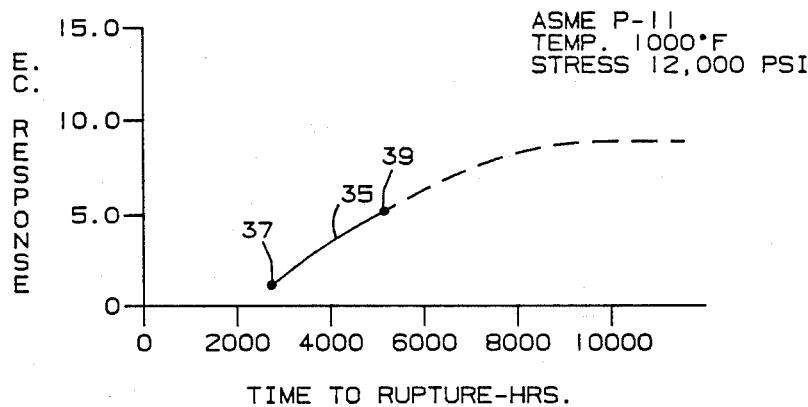

The results of these correlation tests are plotted in FIGS. 4a and 4b. The trace 29 in FIG. 4a provides a correlation between eddy current readings and the minimum creep rate in percent per hour. The point 31 is the data point for the "hot" sample, and 33 represents the data point for the "cold" sample. The broken portion of the trace is an extrapolation of the test data. The trace 35 in FIG. 4b represents the correlation between eddy current response and time to rupture measured in hours. The data point for the "hot" sample is 37 and for the "cold" sample 39. Again, the dashed portion of the trace 35 is an extrapolation of the test data which, as can be seen, becomes asymptotic with increasing time to failure.

With the correlations of FIGS. 4a and b, one can determine from an eddy current response reading, the creep damage to a given workpiece in terms of the % creep rate and the time to failure for the given temperature and stress conditions. Multiple correlation for other temperature and stress conditions for the given material can be developed by conducting creep damage tests on other specimens, so that a full range of correlations are available.

Qualitative measurements can be made by comparing clean surface eddy current responses made at hot and cold locations on the hardware of concern. This simplified approach combined with surface metallography or replication could be most valuable in identifying the most damaged areas to be examined by alternate methods. In both the quantitative and qualitative techniques described above, lowering the eddy current test frequency can be used to more deeply penetrate the metal surface thus providing a more representative test sampling.

The actual test probe configuration; diameter, wire size, number of turns, permanent magnetic rating et cetera, will depend upon the area and depth of penetration associated with the desired hardware scanning requirements. For the exemplary tests, a ⅜ inch diameter coil made of 250 turns of 42 gauge copper wire was used. A cermarian cobalt permanent magnetic was used to provide the magnetic bias, and a Nortec NDT-25 operating at 50 kHz was used as the signal generator and processor. For deeper penetration, lower frequencies would be used.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of determining creep damage in a ferromagnetic workpiece, said method comprising the steps of:
   placing an eddy current coil adjacent to the ferromagnetic workpiece which has been previously subjected to a prolonged period of stress at elevated temperature;
   applying an alternating current signal to said eddy current coil to induce eddy currents in the ferromagnetic workpiece;
   measuring the current passing through said coil as influenced by said workpiece; and
   comparing said current measurement with a current calibrated to known creep damage to determine the creep damage.

2. The method of claim 1 including the step of applying a magnetic bias to said workpiece while the current in said coil is being measured.

3. A method of non-destructive testing of a workpiece composed of a selected ferromagnetic material for creep damage comprising the steps of:
   (a) successively placing an eddy current coil adjacent a selected location on the surface of calibration specimens composed of said selected ferromagnetic material each of which specimen has been previously subjected to different conditions of mechanical stress and elevated temperature;
   (b) supplying an alternating current to the eddy current coil to induce eddy currents in the specimens;
   (c) measuring the current passing through said eddy current coil as influenced by said specimens;
   (d) independently determining the amount of creep damage to each specimen at the selected locations;
   (e) generating correlations for said selected ferromagnetic material between measured current through the eddy current coil and creep damage;
   (f) placing said eddy current coil adjacent a selected location on the surface of said workpiece;
   (g) supplying an alternating current to said eddy current coil to induce eddy currents in said workpiece;
   (h) measuring the current passing through said eddy current coil as influenced by said workpiece; and
   (i) determining the measure of creep damage at the selected location on the workpiece from the measurement of the current in the eddy current coil as influenced by said workpiece and from said correlations.

4. The method of claim 3 including the steps of:
   applying a constant biasing magnetic field to said selected locations on said specimens and on said workpiece.

5. The method of claim 3 wherein said step of independently determining the amount of creep damage to each specimen comprises;
   performing a creep rupture test on the specimen and calculating therefrom the creep damage in terms of the creep rate, and wherein the step of generating said correlations comprises correlating the eddy current measurements with the calculated creep rate for each specimen.

6. The method of claim 3 wherein said step of independently determining the amount of creep damage to each specimen comprises; performing a creep rupture test on the specimen; and calculating therefrom the time to failure of said specimen, and wherein the step of generating said correlations comprises correlating the eddy current measurement with the time to failure for each specimen.

7. A method of determining the location of greatest creep damage in a ferromagnetic workpiece comprising the steps of:
   (a) placing an eddy current coil adjacent a selected location on the surface of a ferromagnetic workpiece which has been previously subjected to stress during prolonged periods of elevated temperature;
   (b) applying an alternating current to said eddy current coil to induce eddy currents in said workpiece;
   (c) measuring the current in said eddy current coil influenced by said workpiece;
   (d) repeating steps a, b, and c for at least one other selected location on the surface of the workpiece;
   (e) identifying the selected location at which the lowest eddy current response is measured as the location of the greatest creep damage.

8. The method of 7 including the step of performing a quantitive creep damage test at said identified location.

9. The method of claim 8 including the additional step of applying a biasing magnetic field to said workpiece at said selected locations while said current measurements are being made.

* * * * *